(12) United States Patent
Dwork

(10) Patent No.: US 9,226,823 B2
(45) Date of Patent: Jan. 5, 2016

(54) VALVE PROSTHESIS

(71) Applicant: Medtronic, Inc., Minneapolis, MN (US)

(72) Inventor: Joshua Dwork, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 336 days.

(21) Appl. No.: 13/658,044

(22) Filed: Oct. 23, 2012

(65) Prior Publication Data

US 2014/0114408 A1  Apr. 24, 2014

(51) Int. Cl.
*A61F 2/24* (2006.01)

(52) U.S. Cl.
CPC .............. *A61F 2/2418* (2013.01); *A61F 2/2436* (2013.01); *A61F 2230/008* (2013.01); *A61F 2230/0013* (2013.01); *A61F 2230/0078* (2013.01); *A61F 2250/0039* (2013.01); *Y10T 29/49405* (2015.01)

(58) Field of Classification Search
CPC ................. A61F 2/24; A61F 2/2412–2/2418; A61F 2250/0014; A61F 2250/0039; A61F 2250/0029; A61F 2/2436
See application file for complete search history.

(56) References Cited

U.S. PATENT DOCUMENTS

| 7,404,824 | B1 | 7/2008 | Webler et al. |
| 7,455,689 | B2 | 11/2008 | Johnson |
| 2006/0058871 | A1 | 3/2006 | Zakay et al. |
| 2006/0064174 | A1 | 3/2006 | Zadno |
| 2006/0259136 | A1 | 11/2006 | Nguyen et al. |
| 2007/0093890 | A1 | 4/2007 | Eliasen et al. |

FOREIGN PATENT DOCUMENTS

| WO | WO2008/029296 | 3/2008 |
| WO | WO2009/024859 | 2/2009 |
| WO | WO2009/053497 | 4/2009 |
| WO | WO2011/002996 | 1/2011 |
| WO | WO2011/057087 | 5/2011 |

OTHER PUBLICATIONS

Pettenazzo, E., et al., "BIOSA bileaflet pericardial valve experimental study in sheep model," cardiovascular Pathology 13 (2004), 207-212.

*Primary Examiner* — Howie Matthews

(57) ABSTRACT

A heart valve prosthesis and delivery systems are provided for replacing a cardiac valve. The heart valve prosthesis includes a self-expanding frame includes a portion having a crimp that provides additional flexibility to the self-expanding frame in the collapsed configuration.

15 Claims, 10 Drawing Sheets

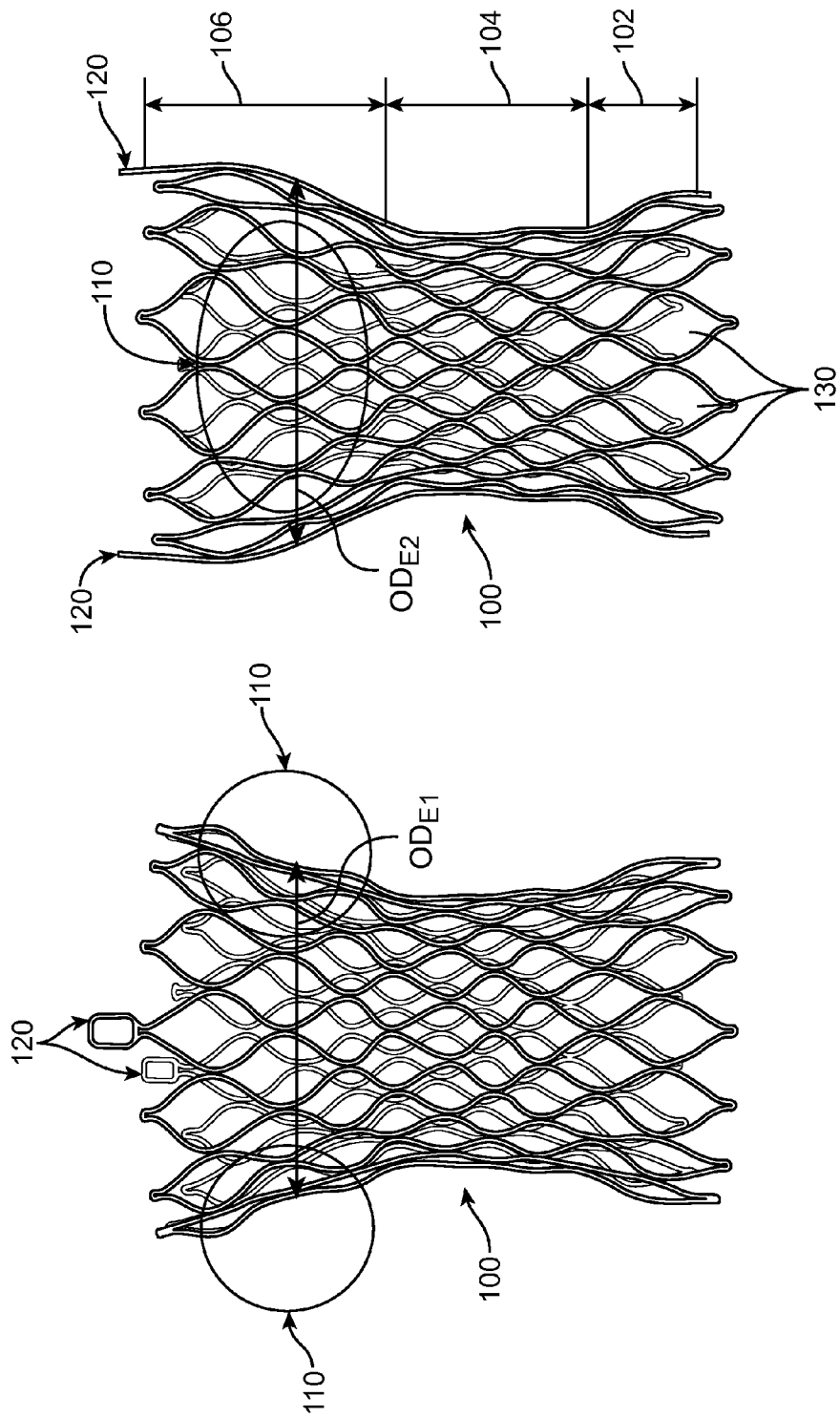

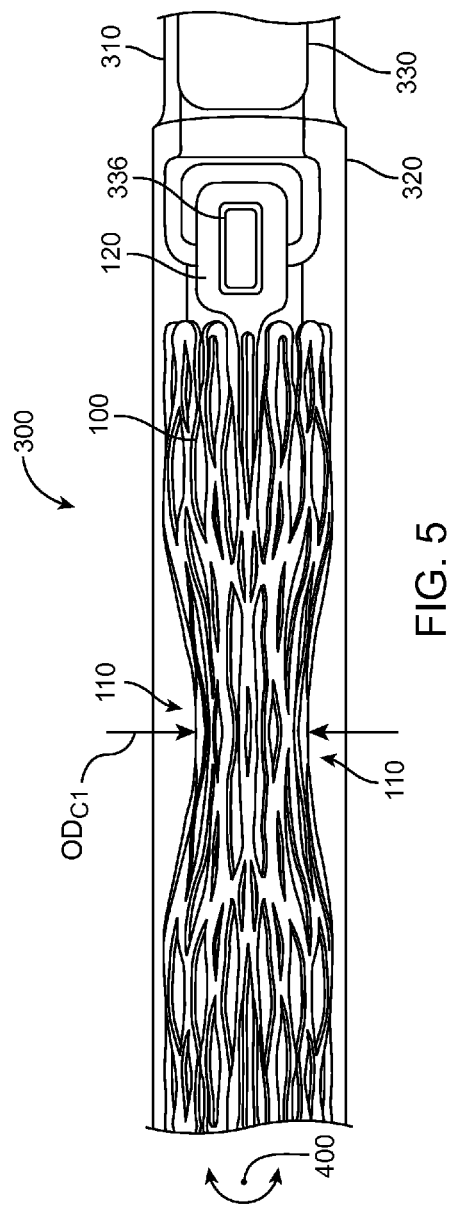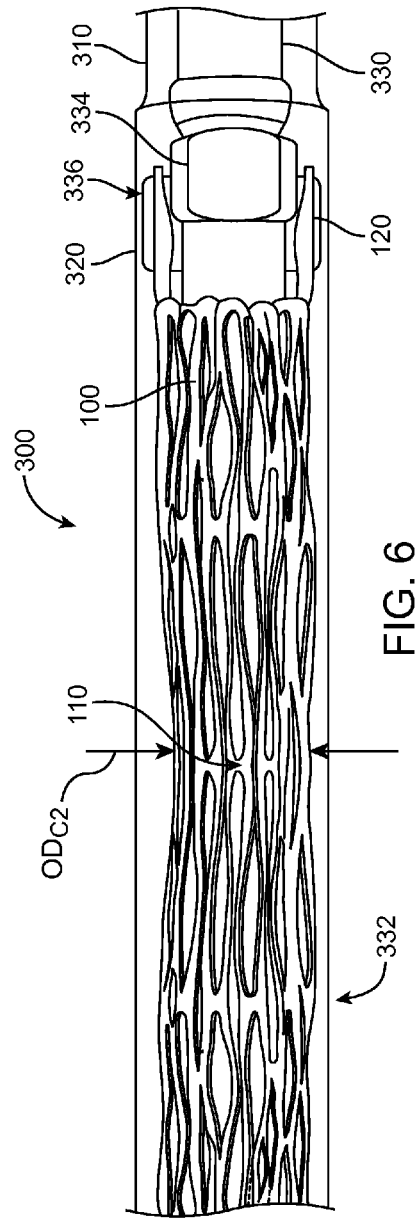

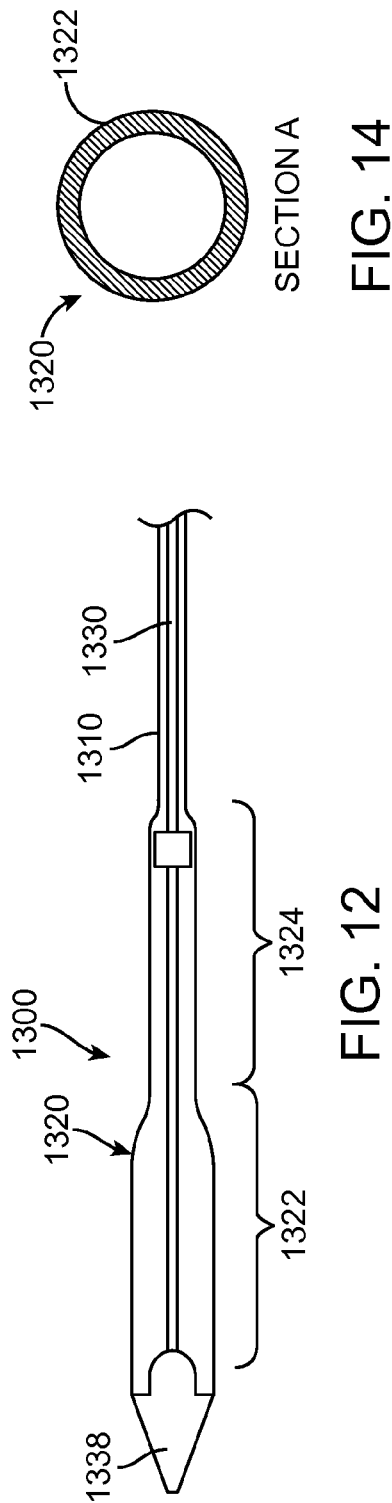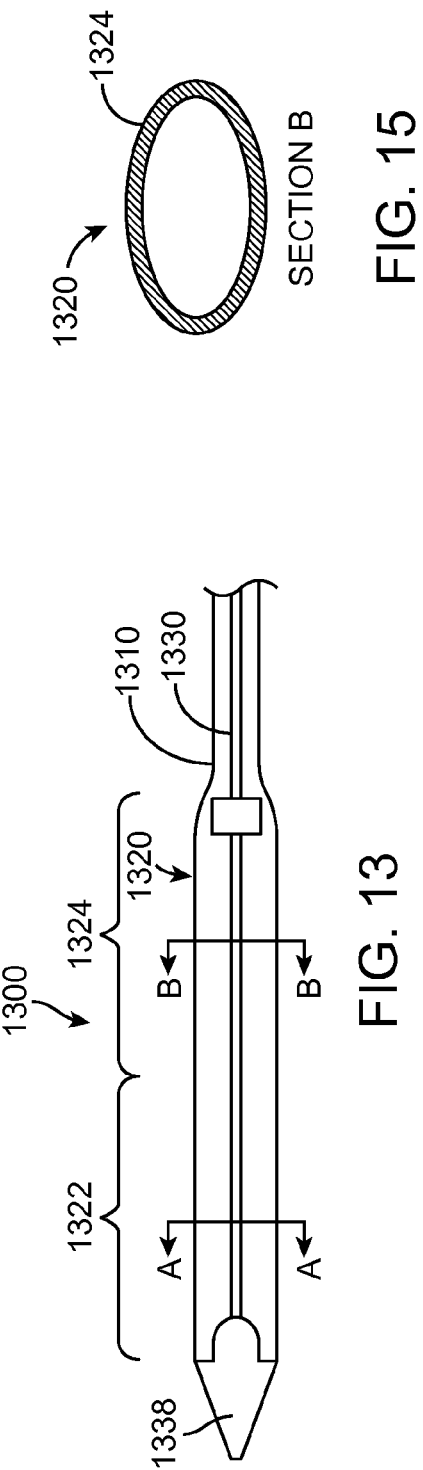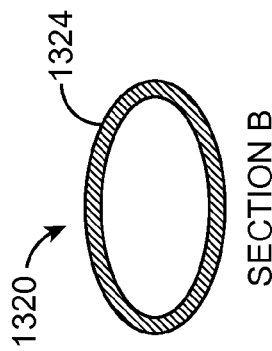

SECTION A

SECTION B

VALVE PROSTHESIS

BACKGROUND OF THE INVENTION

1. Field of the Invention

The present invention is related to an artificial heart valve frame. More specifically, the present invention is directed to an artificial valve prosthesis.

2. Background Art

Cardiac valves exhibit two types of pathologies: regurgitation and stenosis. Regurgitation is the more common of the two defects. Either defect can be treated by a surgical repair. Under certain conditions, however, the cardiac valve must be replaced. Standard approaches to valve replacement require cutting open the patient's chest and heart to access the native valve. Such procedures are traumatic to the patient, require a long recovery time, and can result in life threatening complications. Therefore, many patients requiring cardiac valve replacement are deemed to pose too high a risk for open heart surgery due to age, health, or a variety of other factors. These patient risks associated with heart valve replacement are lessened by the emerging techniques for minimally invasive valve repair, but still many of those techniques require arresting the heart and passing the blood through a heart-lung machine.

Efforts have been focused on percutaneous transluminal delivery of replacement cardiac valves to solve the problems presented by traditional open heart surgery and minimally-invasive surgical methods. In such methods, a valve prosthesis is compacted for delivery in a catheter and then advanced, for example, through an opening in the femoral artery and through the descending aorta to the heart, where the prosthesis is then deployed in the aortic valve annulus.

During delivery, the delivery system including the valve prosthesis must be advanced through multiple bends in the patient's vasculature. Some vascular bends will straighten as the relatively stiff delivery system is passed through. However other vascular bends, e.g. the aortic arch, cannot be straightened. Therefore, a typical delivery system bends in a single plane and kinks, or folds onto itself, when advanced through a substantial vascular bend in order to traverse the bend. This bending of the delivery system is presently routine during delivery of the valve prosthesis frame. Bending of the delivery system allows for a longer valve prosthesis frame that can be anchored in the aortic annulus and the ascending aorta.

A typical valve prosthesis frame is made of self-expanding metals, such as Nitinol. The metal structure of the nitinol holds the compressed frame into a tubular structure which resists bending and kinking. Thus, bending, flexing, and/or kinking the valve prosthesis and delivery system during tracking and delivery typically requires a large amount of bending force.

In view of the foregoing, it would be desirable to provide a valve prosthesis that is capable of conforming to a patient's anatomy while providing a uniform degree of rigidity and protection for critical valve components. Protection for critical valve components is essential to maintain reliability for the valve prosthesis. In addition, it would be desirable to provide a delivery system that facilitates bending of the delivery system around a bend and a valve prosthesis that includes a flexible region that is present when the valve prosthesis is compacted for delivery.

BRIEF SUMMARY

Provided herein are valve prostheses that generally include a self-expanding frame, where the valve prosthesis is sutured to the self-expanding frame. Such configurations achieve numerous goals. For example, such configurations can: prevent the native leaflets from obstructing flow through the left ventricular outflow tract (LVOT); prevent the native leaflets from interacting with the prosthetic leaflets; recruit the native leaflets in minimizing perivalvular leaks; maintain proper alignment of the valve prosthesis; avoid systolic anterior mobility; and maintain valve stability by preventing migration of the valve into the atrium or ventricle.

In view thereof, disclosed herein are aspects of a valve prosthesis which is generally designed to include a frame including a first section having a radially repeating cell pattern and a localized concave depression in a portion of the first section, a second section having a radially repeating cell pattern, and a valve body including a plurality of leaflets attached to the frame in the second section.

In another exemplary embodiment, disclosed herein are aspects of a method of forming a valve prosthesis frame which generally includes providing a heat set mandrel having a circumferential concave portion corresponding to a first section of the valve prosthesis frame, placing the valve prosthesis frame on the heat set mandrel, providing a compression sleeve around the valve prosthesis frame to form a portion of the first section to the circumferential concave portion of the heat set mandrel while a second portion of the first section remains undeformed, and heat treating the valve prosthesis frame to permanently deform the portion of the first section into a localized concave portion.

In another exemplary embodiment, disclosed herein are aspects of a method of treating a valve disorder in a patient's heart which generally includes collapsing a valve prosthesis including a frame having a first section and a second section onto a delivery system, the first section having a localized concave portion and a non-concave portion circumferentially spaced on an axial location of the first section, delivering the delivery system and the valve prosthesis to a heart, expanding the valve prosthesis in the heart, and withdrawing the delivery system from the heart.

BRIEF DESCRIPTION OF THE DRAWINGS/FIGURES

The accompanying figures, which are incorporated herein, form part of the specification and illustrate embodiments of a valve prosthesis frame and delivery system. Together with the description, the figures further serve to explain the principles of and to enable a person skilled in the relevant art(s) to make, use, and implant the valve prosthesis described herein. In the drawings, like reference numbers indicate identical or functionally similar elements.

FIG. 1 is a side view of a valve prosthesis frame according to an aspect of this disclosure.

FIG. 2 is a front view of the valve prosthesis frame shown in FIG. 1 rotated 90 degrees therefrom according to an aspect of this disclosure.

FIG. 5 is a side view of a valve prosthesis frame in a collapsed configuration attached to a delivery system according to an aspect of this disclosure.

FIG. 6 is a front view of the valve prosthesis frame shown in FIG. 5 rotated 90 degrees therefrom, the valve prosthesis frame being shown in a collapsed configuration attached to a delivery system according to an aspect of this disclosure.

FIG. 12 is a side view of a valve prosthesis delivery system according to an aspect of this disclosure.

FIG. 13 is a top view of a valve prosthesis delivery system according to an aspect of this disclosure.

FIG. 14 is a sectional view of a portion of a valve prosthesis delivery system according to an aspect of this disclosure.

FIG. 15 is a sectional view of a portion of a valve prosthesis delivery system according to an aspect of this disclosure.

DETAILED DESCRIPTION OF THE INVENTION

Figure 3:
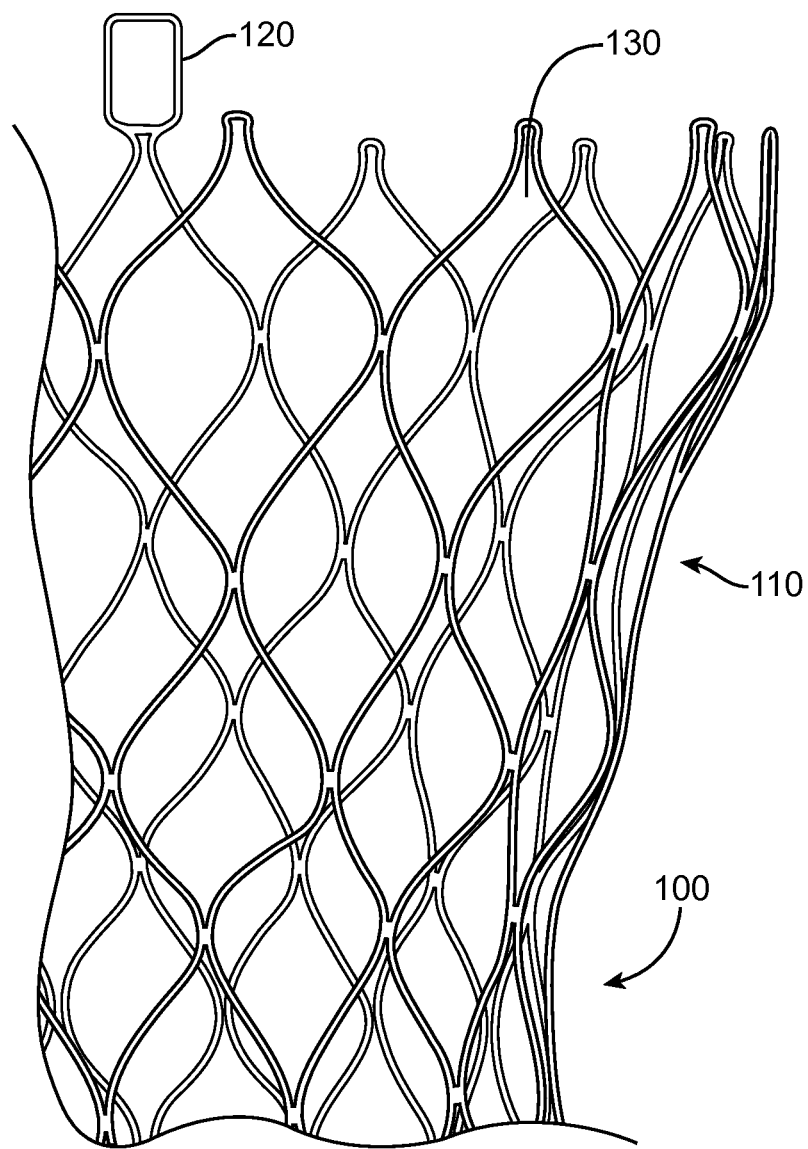
FIG. 3 is a close up side view of a valve prosthesis frame according to an aspect of this disclosure.
Figure 4:
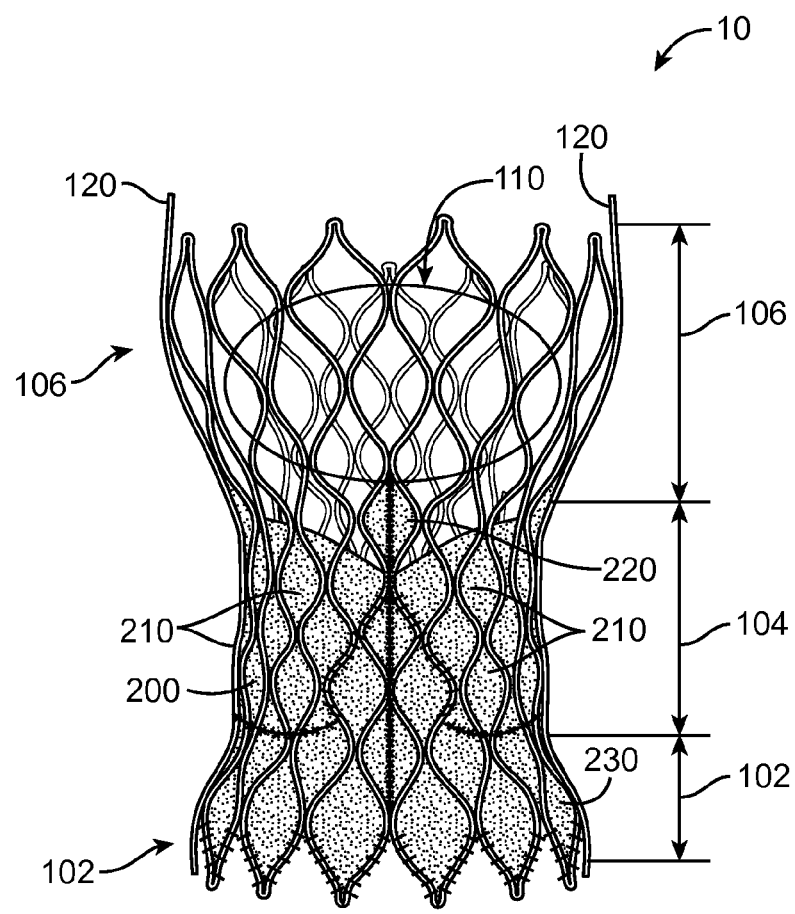
FIG. 4 is a front view of a valve prosthesis according to an aspect of this disclosure.

The following detailed description of a valve prosthesis frame and delivery system refers to the accompanying figures that illustrate exemplary embodiments. Other embodiments are possible. Modifications can be made to the embodiments described herein without departing from the spirit and scope of the present invention. Therefore, the following detailed description is not meant to be limiting.

The present invention is directed to a heart valve prosthesis having a self-expanding frame that supports a valve body. The valve prosthesis can be delivered percutaneously to the heart to replace the function of a native valve. For example, the valve prosthesis can replace a bicuspid or a tricuspid valve such as the aortic, mitral, pulmonary, or tricuspid heart valve.

In one aspect of the invention, the valve body comprises three leaflets that are fastened together at enlarged lateral end regions to form commissural joints, with the unattached edges forming the coaptation edges of the valve. The leaflets can be fastened to a skirt, which in turn can be attached to the frame. The upper ends of the commissure points define an outflow or proximal portion of the valve prosthesis. The opposite end of the valve at the skirt defines an inflow or distal portion of the valve prosthesis. The enlarged lateral end regions of the leaflets permit the material to be folded over to enhance durability of the valve and reduce stress concentration points that could lead to fatigue or tearing of the leaflets. The commissural joints are attached above the plane of the coaptation edges of the valve body to minimize the contacted delivery profile of the valve prosthesis. The base of the valve leaflets is where the leaflet edges attach to the skirt and the valve frame.

Referring now to FIGS. 1-4, frame 100 is an exemplary aspect of the present invention. Frame 100 includes an inflow section 102, a valve section 104, and an outflow section 106. Frame 100 also includes a plurality of cells 130 in the respective sections that can be different sizes and/or shapes. Frame 100 can also include delivery system attachments 120 to connect frame 100 onto a delivery system in a collapsed configuration for delivery into a patient's vasculature. Valve 200 is connected to frame 100 to form valve prosthesis 10. Valve 200 includes leaflets 210, commissures 220, and a skirt 230. In one aspect of the invention, valve 200 is connected to frame 100 in inflow section 102 and valve section 104. The object of the present valve prosthesis is to mimic the native valve structure.

Frame 100 has a total height of approximately 30 mm to approximately 60 mm. In the expanded configuration, the maximum diameter of inflow section 102 can range from about 16 mm to about 36 mm, with a preferred range of about 21 mm to about 33 mm. Inflow section 102 also has a height of approximately 7 mm to approximately 14 mm. The diameter of valve section 104 can range from about 18 mm to about 26 mm, with a preferred range of about 20 mm to about 24 mm. Valve section 104 also has a height of approximately 7 mm to approximately 14 mm. The maximum diameter of outflow section 106 can range from about 28 mm to about 45 mm, with a preferred range of about 30 mm to about 38 mm. Outflow section 106 also has a height of approximately 10 mm to approximately 25 mm.

The plurality of cells 130 forming a cell pattern in frame 100 permit frame 100 to adapt to the specific anatomy of the patient, thereby reducing the risk of valve prosthesis migration and reducing the risk of perivalvular leakage. In one aspect of the invention, inflow section 102 of valve prosthesis 10 is disposed in the aortic annulus of the patient's left ventricle.

Typically, heart valve prostheses aim to create laminar blood flow through the prosthesis in order to prevent lysis of red blood cells, stenosis of the prosthesis, and other thromboembolic complications. Outflow section 106 is designed to conform to a patient's anatomy and to anchor valve prosthesis 10 in the patient's ascending aorta to prevent lateral movement or migration of valve prosthesis 10 due to normal movement of the heart.

In one aspect of the invention, frame 100 includes a crimp, dent, and/or concave depression 110 in a portion of frame 100. The term crimp will be used throughout to refer to the crimp, dent, or concave depression 110. Crimp 110 is provided so that when frame 100 is collapsed onto a delivery system, the region of frame 100 at crimp 110 is flexible around an axis perpendicular to the longitudinal direction. This flexibility permits the frame and delivery system to bend, flex, and/or kink as the frame and delivery system are advanced through a bend in a patient's vasculature. In one aspect of the invention, crimp 110 extends circumferentially across approximately three cells 130 of frame 100. In an alternate aspect of the invention, crimp 110 extends circumferentially across approximately one cell 130 of frame 100 to approximately four cells 130 of frame 100.

The outer diameter of frame 100 is reduced through crimp 110, as shown in FIGS. 1, 3, and 5-6. More particularly, a reduction in the outer diameter of frame 100 due to crimps or localized concave depressions 110 may be understood: by comparing an outer diameter $OD_{E1}$ of expanded frame 100 through crimes 110 in FIG. 1 with an outer diameter $OD_{E2}$ of expanded frame 100 through adjacent segments without crimes in FIG. 2, wherein the adjacent segments are the uncrimped or non-concave portions that circumferentially extend between crimps 110; and by comparing an outer diameter $OD_{C1}$ of collapsed frame 100 through crimes 110 in FIG. 5 with an outer diameter $OD_{C2}$ of collapsed frame 100 through adjacent segments without crimps in FIG. 6, wherein the adjacent segments are the uncrimped or non-concave portions that circumferentially extend between crimps 110. In one aspect of the invention, each crimp 110 reduces the outer diameter $OD_{E1}$, $OD_{C1}$ of frame 100 by approximately 1 mm to approximately 3 mm as compared to an outer diameter of a portion of frame 100 that does not include a crimp 110. In one aspect of the invention, each crimp 110 reduces the outer diameter of frame 100 by approximately 1 mm. In an alternate aspect of the invention, each crimp 110 reduces the outer diameter of frame 100 by approximately 2 mm. In an alternate aspect of the invention, each crimp 110 reduces the outer diameter of frame 100 by approximately 3 mm.

In the expanded configuration, crimp 110 can be difficult to visually notice because the reduction of the outer diameter of frame 100 due to crimp 110 is relatively small compared to the outer diameter of frame 100 in the expanded configuration. Therefore, crimp 110 will not affect the function or placement of valve prosthesis 10 in the patient's anatomy.

However, in the collapsed configuration, shown in FIGS. 5-6, the approximately 1 mm to approximately 3 mm crimp is reduced in diameter while the overall diameter of the frame is reduced to a diameter of approximately 6 mm, or to the size of the inner diameter of the delivery system capsule containing the crimped frame and valve, as shown in FIGS. 5 and 6. Crimp 110 reduces the outer diameter of a portion of frame 100 and in the collapsed configuration, positions the crimped frame portion towards the center of frame 100. In other words, crimp 110 pulls frame 100 material in towards the center of frame 100, closer to the neutral axis of bending. Thus, crimp 110 creates a flexible portion in frame 100 in the collapsed configuration, thus allowing the delivery system and frame to bend, flex, and/or kink in a single plane and traverse a bend in a patient's vasculature during delivery of valve prosthesis 10.

As shown in FIGS. 1-3, crimp 110 can be positioned in outflow portion 106 of frame 100. In an alternate aspect of the invention, crimp 110 can be positioned in any portion of frame 100 to create flexibility at that specific longitudinal location of frame 100. In one aspect of the invention, crimp 110 can be circumferentially spaced approximately 90 degrees from delivery system attachments 120.

In an aspect of the invention, frame 100 can include two crimps 110, as shown in FIG. 1. In this aspect, crimps 110 are circumferentially spaced approximately 180 degrees apart. As such, crimps 110 will facilitate bending, flexing, and/or kinking in a single plane during delivery.

In an alternate aspect of the invention, frame 100 can include three or more crimps 110. In a further aspect of the invention, a plurality of crimps 110 can extend along the circumference of frame 100. In this aspect, crimps 110 create an hourglass shape in frame 100. The hourglass shape allows frame 100 to bend, flex, and/or kink in multiple planes during delivery of valve prosthesis 10. In the aspects of the invention including two crimps 110 circumferentially spaced approximately 180 degrees apart and/or a plurality of crimps 110, each crimp 110 reduces the outer diameter of its respective portion of frame 100 in the expanded configuration and in the collapsed configuration, as depicted by expanded outer diameter $OD_{E1}$ through opposing crimps 110 in FIG. 1 and as depicted by collapsed outer diameter $OD_{C1}$ through opposing crimps 110 in FIG. 5.

In one aspect of the invention, crimp 110 is permanently heat set into frame 100. In an alternate aspect of the invention, crimp 110 is bistable such that crimp 110 is present in the collapsed configuration of frame 100, but is not present in the expanded configuration of frame 100.

Figure 7:
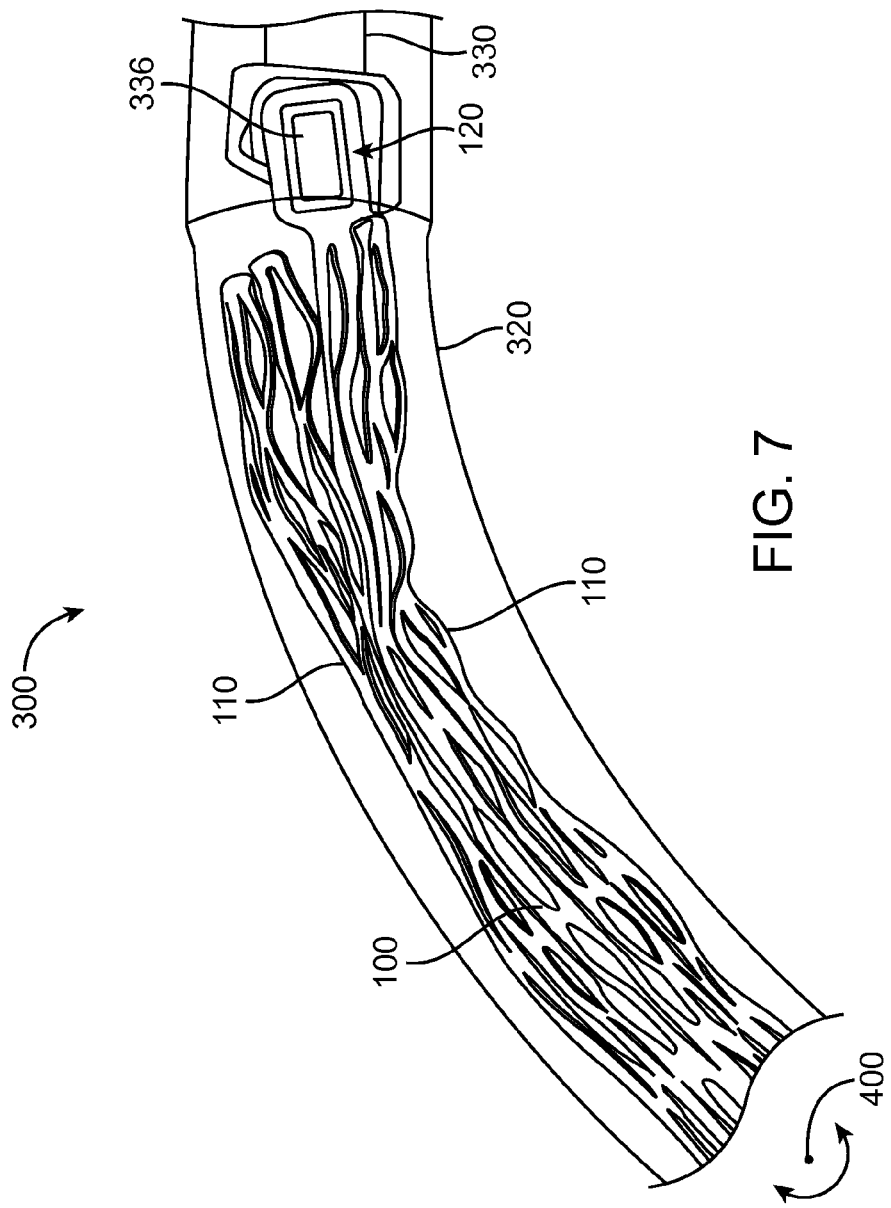
FIG. 7 is a side view of a valve prosthesis frame in a collapsed configuration attached to a delivery system according to an aspect of this disclosure.

As shown in FIGS. 5-7, frame 100 can be collapsed onto a delivery system 300 including a pusher tube 310 and a central tube 330, each of which are concentrically aligned and permit relative motion with respect to each other. At a distal end of pusher tube 310 is a capsule 320 that surrounds the collapsed valve prosthesis 10 during delivery to the implantation site. The capsule 320 restrains valve prosthesis 10 in the radial direction. During deployment, the capsule is withdrawn over the valve prosthesis.

At a distal end of central tube 330 is a plunger assembly 332 which includes a hub 334, a tip 338, and attachment tabs 336. Tip 338 facilitates the advancement of delivery system 300 through the patient's vasculature. Hub 334 includes one or more attachment tabs 336 for retaining valve prosthesis 10 on plunger assembly 332. Tabs 336 also prevent the pre-release of valve prosthesis 10 and assist in retaining valve prosthesis 10 during recapture.

In the collapsed configuration, frame 100 attachments 120 connect onto attachment tabs 336 on delivery system 300. Collapsed frame 100 abuts the interior surface of capsule 320 and is thus maintained in a collapsed configuration on delivery system 300. As shown, crimp 110 facilitates bending, flexing, and/or kinking of frame 100 around axis 400.

Figure 8:
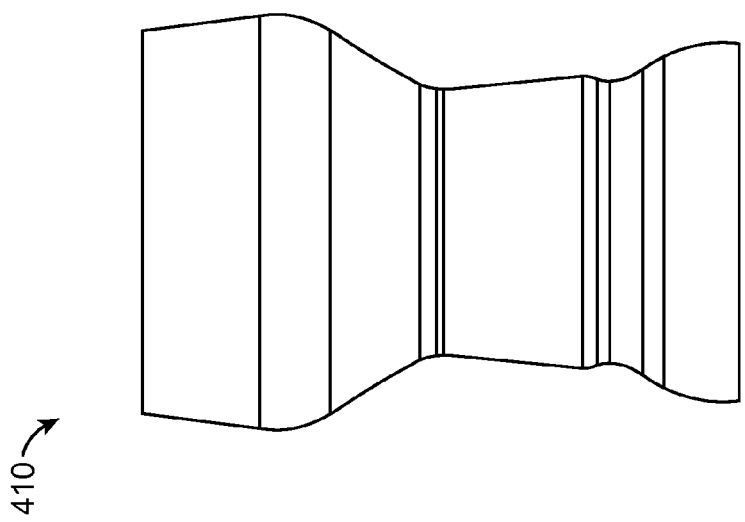
FIG. 8 is a front view of a heat set mandrel.
Figure 9:
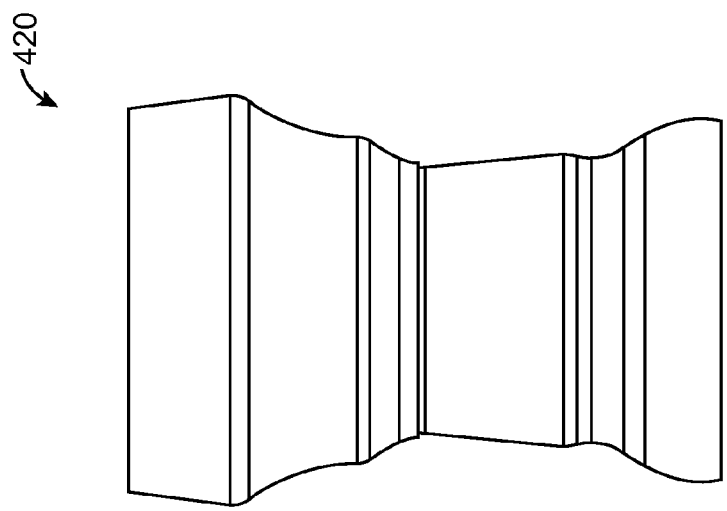
FIG. 9 is a front view of a crimped frame mandrel according to an aspect of this disclosure.
Figure 11:
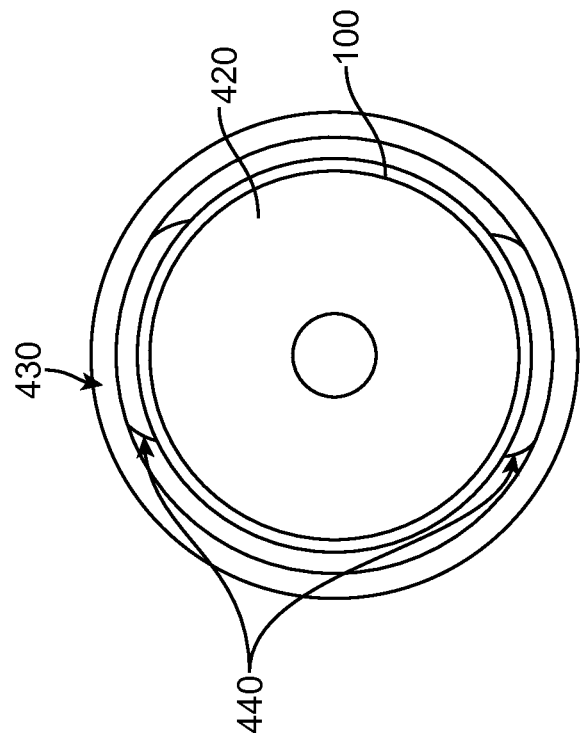
FIG. 11 is a top view of a crimped frame mandrel and compression sleeve according to an aspect of this disclosure.
Figure 10:
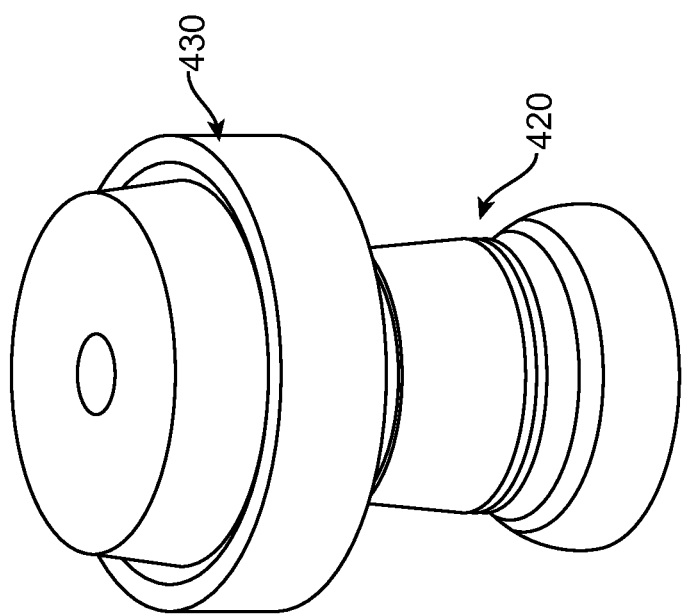
FIG. 10 is a perspective view of a crimped frame mandrel and compression sleeve according to an aspect of this disclosure.

Manufacture of frame 100 will now be described. Frame 100 can be laser cut from a solid tube of a self-expanding metal, such as Nitinol, with a thin wall thickness. The laser cuts cells 130 into the nitinol tube forming a cell pattern. After laser cutting is complete, the nitinol tube is expanded to increase the overall size and diameter of the nitinol tube. Nitinol is formable when it is brought to a cold temperature. Therefore, to expand the nitinol tube, the nitinol tube is brought to a cold temperature and a cylindrical expansion mandrel is inserted into the formable nitinol tube. The expanded nitinol tube is then subject to a high temperature greater than 500 degrees centigrade. This high temperature cycle removes the stress and strain in the nitinol tube and effectively creates a new natural state for the expanded nitinol tube. This expansion cycle is repeated several times with larger expansion mandrels, each expansion step being within the strain limits of the nitinol material. For the final expansion step, a shaped mandrel is inserted into the expanded nitinol tube. A typical shaped mandrel 410 is shown in FIG. 8. Shaped mandrel 410 has the shape of a finished frame. Referring now to FIGS. 9-11, mandrel 420 has a concave section machined into it to allow for creation of crimp 110. Mandrel 420 is inserted into frame 100 and compression sleeve 430 is placed around the concave section on mandrel 420. Compression spacers 440 are inserted in between compression sleeve 430 and frame 100 to force a portion of frame 100 into the concave section of mandrel 420. After a final high temperature cycle, frame 100 maintains the shape of mandrel 420 including crimp 110 formed by the concave section of mandrel 420 and compression spacers 440. Frame 100 then undergoes finishing processing and a valve 200 is sewn to frame 100.

FIGS. 12-15 illustrate an alternate delivery system design directed to facilitate bending, flexing, and/or kinking as the frame and delivery system are advanced through a bend in a patient's vasculature. Delivery system 1300 includes a capsule 1320 having a first portion 1322 having a circular cross-section and a second portion 1324 having an ovaled cross-section. In one aspect of the invention, delivery system 1300 can be used with a frame that does not include a crimp. Instead of a crimp, the ovaled cross-section in second portion 1324 brings frame material closer towards the center of the frame and thus creates a flexible region in the frame. In other words, the ovaled cross section pulls frame material in towards the center of the frame, closer to the neutral axis of bending. Thus, the ovaled cross-section in second portion 1324 creates a flexible portion in the frame in the collapsed configuration, thus allowing the delivery system and frame to bend, flex, and/or kink in a single plane and traverse a bend in a patient's vasculature during delivery of valve prosthesis 10.

Figure 16:
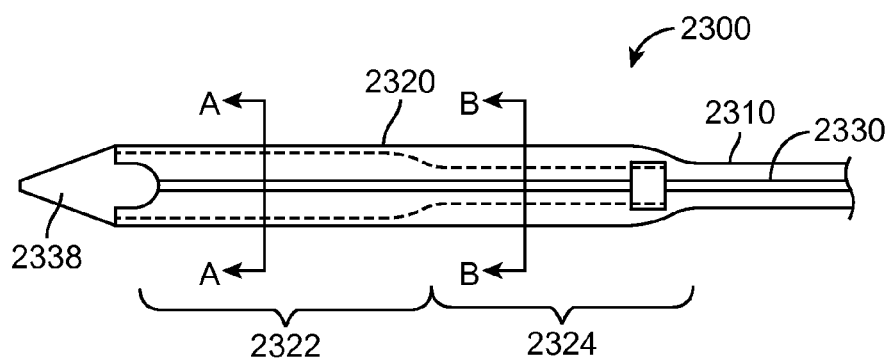
FIG. 16 is a side view of a valve prosthesis delivery system according to an aspect of this disclosure.
Figure 17:
FIG. 17 is a sectional view of a portion of a valve prosthesis delivery system according to an aspect of this disclosure.
Figure 18:
FIG. 18 is a sectional view of a portion of a valve prosthesis delivery system according to an aspect of this disclosure.
Figure 19:
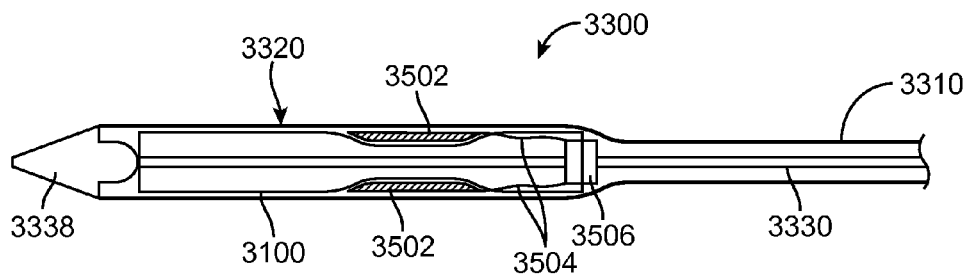
FIG. 19 is a schematic view of a valve prosthesis delivery system according to an aspect of this disclosure.
Figure 20:
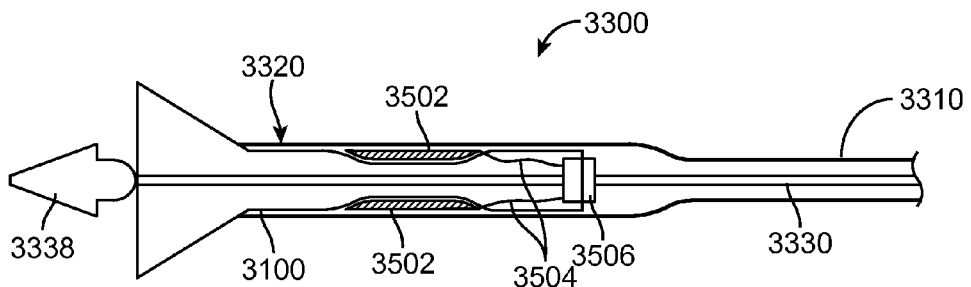
FIG. 20 is a schematic view of a valve prosthesis delivery system according to an aspect of this disclosure.

FIGS. 16-18 illustrate an alternate delivery system design directed to facilitate bending, flexing, and/or kinking as the frame and delivery system are advanced through a bend in a patient's vasculature. Delivery system 2300 includes a capsule 2320 having a first portion 2322 having an inner diameter with a circular cross-section and a second portion 2324 having an inner diameter with an ovaled cross-section. The outer diameter of first portion 2322 is equal to the outer diameter of second portion 2324. In one aspect of the invention, delivery system 2300 can be used with a frame that does not include a crimp. Instead of a crimp, the ovaled cross-section in the inner diameter of second portion 2324 brings frame material closer towards the center of the frame and thus creates a flexible region in the frame. In other words, the ovaled cross section pulls frame material in towards the center of the frame, closer to the neutral axis of bending. Thus, the ovaled cross-section in the inner diameter of second portion 2324 creates a flexible portion in the frame in the collapsed configuration, thus allowing the delivery system and frame to bend, flex, and/or kink in a single plane and traverse a bend in a patient's vasculature during delivery of valve prosthesis 10.

FIGS. 19-22 illustrate an alternate delivery system design directed to facilitate bending, flexing, and/or kinking as the frame and delivery system are advanced through a bend in a patient's vasculature. Delivery system 3300 includes a capsule 3320 attached to the distal end of pusher tube 3310. Hub 3506 is attached to a distal end of central tube 3330 and is attached to spacer tethers 3504 which are in turn attached to spacers 3502. In one aspect of the invention, frame 3100 does not include a crimp. Spacers 3502 are placed on opposite sides of frame 3100 in the collapsed configuration. Thus, instead of a crimp, delivery system 3300 uses spacers 3502 to bring frame material closer towards the center of frame 3100 and thus create a flexible region in frame 3100. In other words, spacers 3502 pull frame material 3100 in towards the center of frame 3100, closer to the neutral axis of bending. Thus, spacers 3502 create a flexible portion in the frame in the collapsed configuration, thus allowing the delivery system and frame to bend, flex, and/or kink in a single plane and traverse a bend in a patient's vasculature during delivery of valve prosthesis 10.

Figure 21:
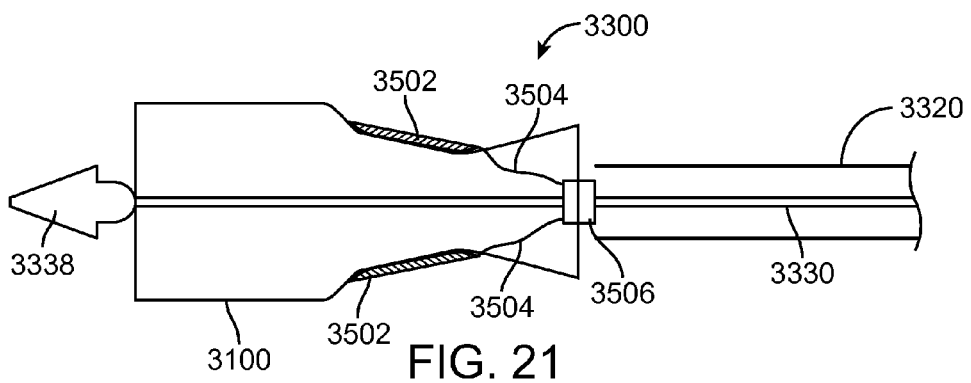
FIG. 21 is a schematic view of a valve prosthesis delivery system according to an aspect of this disclosure.
Figure 22:
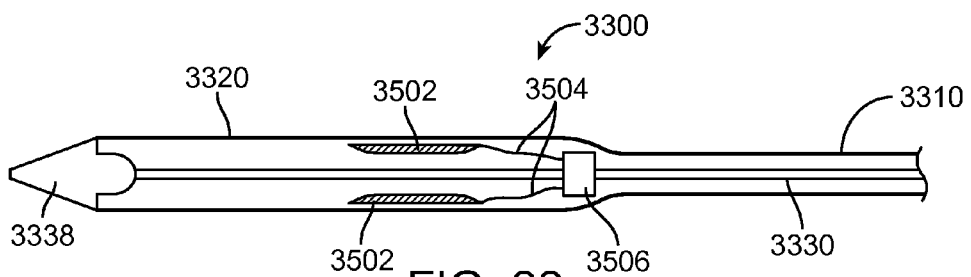
FIG. 22 is a schematic view of a valve prosthesis delivery system according to an aspect of this disclosure.

During deployment of valve prosthesis 3100, capsule 3320 is withdrawn proximally over frame 3100, spacers 3502, and central tube 3330. Spacers 3502 are not attached to capsule 3320. Therefore the shape of frame 3100 including the flexible region imparted by spacers 3502 does not change during capsule 3320 withdrawal. As shown in FIGS. 21-22, after frame 3100 is fully deployed, spacer tethers 3504 allow spacers 3502 to be retracted back into capsule 3320.

The valve prosthesis can replace the function of a tricuspid or bicuspid heart valve including the mitral valve, the aortic valve, the pulmonary valve, or the tricuspid valve. The valve can be delivered, for example, transfemorally, transeptally, transapically, transradially, or transatrially.

Implantation of the valve prosthesis will now be described. As discussed above, the valve prosthesis preferably comprises a self-expanding frame that can be compressed to a contracted delivery configuration onto an inner member of a delivery catheter. This frame design requires a loading system to crimp valve prosthesis 10 to the delivery size, while allowing the proximal end of valve prosthesis 10 to protrude from the loading system so that the proximal end can be attached to tabs 336.

The valve prosthesis and inner member can then be loaded into a delivery sheath of conventional design. The delivery catheter and valve prosthesis can then be advanced in a retrograde manner through the femoral artery and into the patient's descending aorta. The catheter then is advanced, under fluoroscopic guidance, over the aortic arch, through the ascending aorta and mid-way across the defective aortic valve. Once positioning of the catheter is confirmed, capsule 320 can be withdrawn proximally, thereby permitting valve prosthesis 10 to self-expand.

As the valve prosthesis expands, it traps the leaflets of the patient's defective aortic valve against the valve annulus, retaining the native valve in a permanently open state. The outflow section of the valve prosthesis expands against and aligns the prosthesis within the ascending aorta, while the inflow section becomes anchored in the aortic annulus of the left ventricle, so that the skirt reduces the risk of perivalvular leaks.

Alternatively, the valve prosthesis can be delivered through a transapical procedure. In a transapical procedure, a trocar or overtube is inserted into the left ventricle through an incision created in the apex of a patient's heart. A dilator is used to aid in the insertion of the trocar. In this approach, the native valve (e.g. the mitral valve) is approached from the downstream relative to the blood flow. The trocar is retracted sufficiently to release the self-expanding valve prosthesis. The dilator is preferably presented between the valve leaflets. The trocar can be rotated and adjusted as necessary to properly align the valve prosthesis. The dilator is advanced into the left atrium to begin disengaging the proximal section of the valve prosthesis from the dilator.

In an alternate aspect of the invention, the valve prosthesis can be delivered through a transatrial procedure. In this procedure, the dilator and trocar are inserted through an incision made in the wall of the left atrium of the heart. The dilator and trocar are advanced through the native valve and into the left ventricle of heart. The dilator is then withdrawn from the trocar. A guide wire is advanced through the trocar to the point where the valve prosthesis comes to the end of the trocar. The valve prosthesis is advanced sufficiently to release the self-expanding frame from the trocar. The trocar can be rotated and adjusted as necessary to properly align the valve prosthesis. The trocar is completely withdrawn from the heart such that the valve prosthesis self-expands into position and assumes the function of the native valve.

The foregoing description has been presented for purposes of illustration and enablement, and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:
1. A valve prosthesis comprising:
   a frame including:
      a first section having a radially repeating cell pattern, the first section having a single localized concave depres- sion formed therein that circumferentially spans only a portion of a circumference of the first section, and a second section having a radially repeating cell pattern; and a valve body including a plurality of valve leaflets attached to the frame in the second section.

2. A valve prosthesis comprising:

a frame including:

a first section having a radially repeating cell pattern, the first section having first and second localized concave depressions, and a second section having a radially repeating cell pattern; and a valve body including a plurality of valve leaflets attached to the frame in the second section, wherein in the first section the second localized concave depression is circumferentially spaced approximately 180 degrees from the first localized concave depression with non-concave portions of the first frame circumferentially extending there between.

3. The valve prosthesis of claim 1, wherein in a collapsed configuration, an outer diameter of the first section through the concave depression is smaller than an outer diameter of the second section.

4. The valve prosthesis of claim 1, wherein the portion of the circumference of the first section that is spanned by the concave depression consists of a cell of the first section radially repeating cell pattern.

5. The valve prosthesis of claim 1, wherein the portion of the circumference of the first section that is spanned by the concave depression consists of three cells of the first section radially repeating cell pattern.

6. The valve prosthesis of claim 1, wherein the concave depression is formed by deforming and heat setting the portion of the circumference of the outflow section.

7. The valve prosthesis of claim 1, wherein in a collapsed configuration, the concave depression reduces the bending moment of the valve prosthesis.

8. The valve prosthesis of claim 2, wherein the first localized concave depression does not extend circumferentially to the second localized concave depression.

9. The valve prosthesis of claim 3, wherein in an expanded configuration the outer diameter of the first section through the concave depression is greater than an outer diameter of the second section.

10. The valve prosthesis of claim 1, wherein an outer diameter of the first section is reduced at the location of the concave depression.

11. The valve prosthesis of claim 2, wherein in a collapsed configuration an outer diameter of the first section through the first and second localized concave depressions is smaller than an outer diameter of the first section through the non-concave portions there between.

12. The valve prosthesis of claim 2, wherein in a collapsed configuration an outer diameter of the first section through the first and second localized concave depressions is smaller than an outer diameter of the second section.

13. The valve prosthesis of claim 2, wherein each of the first and second localized concave depressions circumferentially spans a respective cell of the first section radially repeating cell pattern.

14. The valve prosthesis of claim 2, wherein each of the first and second localized concave depressions circumferentially spans three cells, respectively, of the first section radially repeating cell pattern.

15. The valve prosthesis of claim 2, wherein in an expanded configuration an outer diameter of the first section through the first and second localized concave depressions is greater than an outer diameter of the second section.

* * * * *